(12) United States Patent
Ou (10) Patent No.: US 6,232,518 B1
(45) Date of Patent: *May 15, 2001

(54) REMOVAL OF BENZENE FROM ORGANIC STREAMS USING CYCLODEXTRINS

(75) Inventor: Di-Yi (John) Ou, Houston, TX (US)

(73) Assignee: Exxon Mobil Chemical Patents Inc., Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/888,224

(22) Filed: Jul. 3, 1997

(51) Int. Cl.[7] ..................................... C07C 7/152
(52) U.S. Cl. .............................. 585/864; 585/801; 585/2; 585/3; 210/909; 210/702; 210/710; 210/711
(58) Field of Search ..................................... 585/864, 804, 585/2, 3; 210/909, 702, 710, 711

(56) References Cited

U.S. PATENT DOCUMENTS

| | | | | |
|---|---|---|---|---|
| 3,456,028 | * | 7/1969 | Gerhold et al. | 585/802 |
| 3,465,055 | * | 9/1969 | Gleim et al. | 536/103 |
| 3,472,835 | * | 10/1969 | Buckler et al. | 536/46 |
| 4,426,292 | * | 1/1984 | Wernick et al. | 210/635 |
| 5,095,173 | * | 3/1992 | Uemasu et al. | 585/865 |
| 5,177,302 | * | 1/1993 | Uemasu et al. | 585/864 |
| 5,200,517 | * | 4/1993 | Uemasu et al. | 536/103 |

FOREIGN PATENT DOCUMENTS

| | | | |
|---|---|---|---|
| 4238430 | * | 5/1994 | (DE) . |
| 42 38 430 A1 | | 5/1994 | (DE) . |
| 0487818A1 | | 6/1992 | (EP) . |

OTHER PUBLICATIONS

Chemical Abstracts, vol. 84, No. 19, May 10, 1976, Columbus, Ohio, US; abstract No. 135074g, p. 449; XP002077719.
PCT US98/13403 International Search Report.

* cited by examiner

Primary Examiner—Walter D. Griffin (57) ABSTRACT

A method for separating benzene from a hydrocarbon mixture containing benzene and at least one other organic material is carried out by treating the hydrocarbon mixture with at least one cyclodextrin to form complexes of the cyclodextrin with at least a portion of the benzene present in the hydrocarbon mixture. The cyclodextrin-benzene complexes then are separated from the hydrocarbon mixture.

47 Claims, 4 Drawing Sheets

FIG. 1

MOLECULAR STRUCTURE OF CYCLODEXTRINS
* SECONDARY -OH GROUPS OF C-2 AND C-3
PRIMARY -OH GROUPS OF C-6

REMOVAL OF BENZENE FROM ORGANIC STREAMS USING CYCLODEXTRINS

FIELD OF THE INVENTION

The present invention relates to methods for separating benzene from mixtures of other hydrocarbons, and recovering a high concentration of benzene from such mixtures. In particular, the invention relates to a method for removing and recovering a high concentration of benzene from gasoline or reformate using cyclodextrins as complexing agents.

BACKGROUND OF THE INVENTION

Benzene is a highly carcinogenic compound which either is found in or produced during the processing of many hydrocarbon streams. One hydrocarbon substrate or stream in which benzene is found is motor gasoline. In an attempt to reduce pollution from automobile exhaust, environmental regulations have been passed in the United States and in other countries setting limits on the amount of benzene that can exist in motor gasoline in order for the sale of that gasoline to be legal. These regulations can be met only if benzene is removed either from the motor gasoline, itself, or from reformate, which is a major source of the benzene found in motor gasoline.

A typical reformate contains in the range of from about 2–4 wt % benzene in a mixture of paraffins, olefins, naphthenes, toluene, xylenes, ethylbenzene (EB), 9-carbon aromatics (A9s), 10-carbon aromatics (A10s), and other heavy hydrocarbons. Currently, no economically satisfactory technology is capable of directly removing benzene from such a mixture. Existing processes require the use of an expensive benzene heart-cut distillation column, which makes a C6–C7+split of the reformate, producing an overhead stream of 20–30% benzene and 70–80% non-aromatics. The heart-cut benzene stream then must be treated using other known methods, such as adsorption, extraction, etc., to produce high purity benzene or other benzene products.

An economically efficient method is needed for directly removing benzene from hydrocarbon substrates, such as reformate and/or motor gasoline.

SUMMARY OF THE INVENTION

The present invention provides a method of separating benzene from a hydrocarbon mixture comprising providing a mixture comprising benzene and at least one other hydrocarbon, treating said mixture with a complexing agent comprising at least one cyclodextrin in an amount and under conditions effective to form complexes comprising said cyclodextrin and at least a portion of said benzene, and separating said complexes from said mixture.

DERAILED DESCRIPTION OF THE INVENTION

The present invention is directed to the removal of benzene from mixtures of one or more different organic materials. As used in this application, the term "organic materials" includes, but is not necessarily limited to unrefined and refined hydrocarbon products, including natural gas, derived from petroleum or from the liquefaction of coal. Thus, particularly for petroleum based fuels, the term "organic materials" includes, but is not necessarily limited to wellhead condensate as well as crude oil which may be contained in storage facilities at the producing field. "Organic materials" also includes the same materials transported from those facilities by barges, pipelines, tankers, or trucks to refinery storage tanks, or, alternately, transported directly from the producing facilities through pipelines to the refinery storage tanks. The term "organic materials" also includes refined products, interim and final, produced in a refinery, including distillates such as gasolines, distillate fuels, oils, and residual fuels. Preferred organic materials are those in the gasoline boiling range, which is generally considered to be in the range of from about 80–400° F. Suitable hydrocarbon mixtures include, but are not necessarily limited to reformate, hydrocrackate, pyrolysis gasoline, and FCC (fluid catalytic cracker) naptha. A preferred organic material is reformate.

Figure 1:
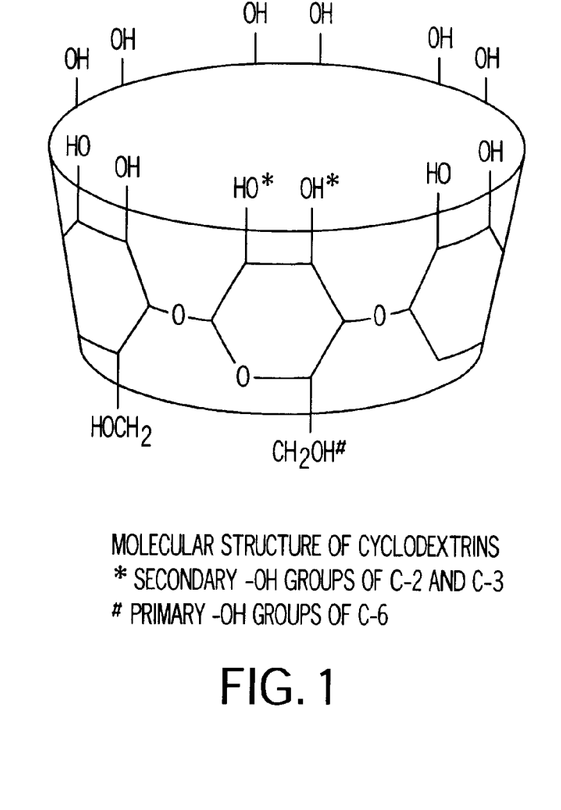
FIG. 1 is a schematic representation of a cyclodextrin.

Benzene is removed from the organic materials using one or more cyclodextrins. Cyclodextrins (CD) are oligomers of glucose in which the glucose building blocks are linked together in a ring-shape like a doughnut, as depicted in FIG. 1. The inner diameter of the "doughnut" varies depending upon the number of glucose units in the ring: "α-CD" has 6 glucose units and the ring has an inner diameter of 5.1±0.6 Å; "β-CD" has 7 glucose units and the ring has an inner diameter of 7.2±0.6 Å; and, γ-CD has 8 glucose units and the ring has an inner diameter of 8.9±0.6 Å.

The cyclodextrin ring has two different types of hydroxyl groups bonded around its upper and lower rims. Secondary hydroxyl groups are bonded to the ring at the C-2 and C-3 positions, which are on the upper, larger rim of the CD ring. A primary hydroxyl group is bonded via a hydroxymethylene group to C-6 of the glucose ring, which is located around the lower, smaller rim of the CD ring. The upper and lower rims of the CD ring become very hydrophilic due to the presence of these hydroxyl groups. In contrast, the inner surface of the CD ring is lined with relatively apolar methylene groups and oxygen groups. These groups make the inner surface of the CD ring more organophilic (or hydrophobic). CD rings are soluble in many polar solvents, including water, and have chemical and physical properties that can be modified by derivatization of the hydroxyl groups.

According to the present invention, benzene is encapsulated inside of the CD ring, forming a CD-benzene complex which is immiscible in the hydrocarbon mixture and can be separated from the hydrocarbon mixture relatively easily.

Substantially any unsubstituted α-cyclodextrin should work in the present invention. α-cyclodextrins and derivatives thereof bearing a substituent defined below at the primary hydroxyl group in the C-6 position ("C-6 derivatives") show particular selectivity toward benzene and paraffinic/olefinic molecules with small critical diameters including linear paraffins, mono-branched paraffins, linear olefins, monobranched olefins, naphthenes, such as cyclopentane, methyl-cyclopentane, cyclohexane, methyl-cyclohexane, 1,4-dimethyl cyclohexane, etc., over those hydrocarbons with larger critical diameter, including aromatics, multi-branched paraffins and olefins, 1–2 and 1–3 substituted naphthenes. Unsubstituted β- and γ-cyclodextrins and derivatives thereof substituted at the C6 position show selectivity toward benzene over other hydrocarbons, including paraffins, naphthenes, olefins, and aromatics.

The benzene encapsulation using α-cyclodextrins is believed to involve both steric and electronic interactions. The benzene molecule has relatively small critical dimensions (3.4 Å×6.2 Å), as does α-cyclodextrin. The small size of the benzene molecule allows the benzene molecule to insert itself more easily into the α-cyclodextrin ring than compounds which have larger critical dimensions (e.g., toluene, xylenes, and other aromatics and naphthenes). α-, β-, and γ-CD's also may interact with encapsulated materials via the weakly polarized oxygen groups found at the inner surface of the α-CD ring. The electron structure of benzene could give rise to the selectivity of cyclodextrins toward benzene as opposed to smaller, and/or less polar compounds, such as n-hexane (3.9 Å×4.3 Å), n-heptane, cyclohexane, etc.

The selective encapsulation of benzene can be accomplished using either a pure CD or a mixture of two or more CDs. The CD's may be substituted on the C-6 primary hydroxyl group or on the C-2 and/or C-3 secondary hydroxyl groups with a substituent selected from the group consisting of glucosyl groups, maltosyl groups, maltooligosaccharide residues, hydroxyalkyl groups, sulfur-containing groups, such as alkylenesulfonic groups, sulfonic groups, deoxymercapto-groups, etc., carboxyalkyl groups, methyl groups, acylated groups, such as acetyl, succinyl, lauryl, etc., silyl groups, such as dimethylsilyl groups, butyldimethylsilyl groups, etc., halogenated groups, such as deoxychloro groups, deoxybromo groups, etc., nitrogen-containing groups, such as amino groups, alkylamino groups, acido groups, etc., and inorganic acid esters.

Preferred CD's for use in encapsulating benzene will depend upon the particular hydrocarbon substrate being treated and upon the objective of the removal process. For example, if the prime objective is to remove benzene from a hydrocarbon substrate, and if the final product may comprise a mixture of benzene and paraffins, preferred CD's are α-, β-, and γ-CD derivatives, most preferably α-CD derivatives, bearing one of the foregoing substituents at the C-6 position. Such CD's are highly selective to benzene and paraffins, whose molecular size matches closely with the CD opening.

If the objective of the operation is to remove benzene from motor gasoline and also to produce a high concentration benzene product, preferred CD's would be selected from the group consisting of β-, and γ-CD derivatives with the hydroxyl group at the C-6 position substituted with at least one member selected from the group consisting of glucosyl groups, maltosyl groups, maltooligosaccharide residues, hydroxyalkyl groups, sulfur-containing groups, such as alkylenesulfonic groups, sulfonic groups, deoxymercapto- groups, etc., carboxyalkyl groups, methyl groups, acylated groups, such as acetyl, succinyl, lauryl, etc., silyl groups, such as dimethylsilyl groups, butyldimethylsilyl groups, etc., halogenated groups, such as chloro groups, bromo groups, iodo groups, deoxychloro groups, etc., nitrogen-containing groups, such as amino groups, alkylamino groups, acido groups, etc., and inorganic acid esters, and combinations thereof.

Many suitable derivatized CD's are available from commercial sources, such as the following: monoglucosyl-α-CD, and monomaltosyl-α-CD, hydroxypropyl-α-CD, hydroxyethyl-α-CD, carboxymethyl-α-CD, hydroxypropyl-β-CD, hydroxyethyl-β-CD, carboxymethyl-β-CD, carboxyethyl-β-CD, methyl-β-CD, glucosyl-β-CD, and maltosyl-β-CD are available from Ensuiko Sugar Co. (Yokohama, Japan), CTD, Inc. (Gainesville, Fla.), Aldrich Chemical Co. (Milwaukee, Wis.), Cerestar USA (Hammon, Ind.), and Wacker Chemical (Adrian, Mich.).

The hydrocarbon mixture may be treated with the CD's in a number of ways. For example, the CD's may be formed as particles of cyclodextrin polymers or may be bound to porous solid particles, and the particles may be used in a packed bed process, such as a fixed bed or a simulated moving bed process. The CD may be used in solution in a suitable solvent in a gas-liquid absorption process or in a liquid-liquid extraction process. Alternately, the hydrocarbon mixture may be passed through a film or membrane comprising cyclodextrins bound to organic or inorganic films or membranes, or a film or membrane comprising polymers of cyclodextrins, in any membrane or filtration process. In a preferred embodiment, the CD's are used as an extracting agent dissolved in any suitable solvent for gas-liquid absorption or liquid-liquid extraction processes. Solvents suitable for such applications include polar solvents, such as water, dimethylsulfoxide (DMSO), sulfolane, dimethylformamide, acetonitrile, tetraethyleneglycol, etc., and mixtures thereof A preferred embodiment, which improves the selectivity of the CD towards benzene, uses a mixture of water and one of the foregoing organic solvents, preferably at a ratio of in the range of from about 60–100 wt % water to 0–40 wt % organic solvent. A preferred mixture is 60 wt % water and 40 wt % organic solvent.

Theoretically, it would be possible to simply feed a low benzene concentration feed directly into a CD extraction unit and to separate and decompose the benzene/CD complexes to recover a high purity, or at least a high concentration benzene product. As a practical matter, such a process would require huge equipment, which would render the process commercially non-viable. For the process to be commercially viable, several steps must be performed to remove hydrocarbons besides benzene from the feed stream. It will be most informative to first examine a typical high purity benzene production process and then to examine how the process can be simplified using cyclodextrins.

Figure 2:
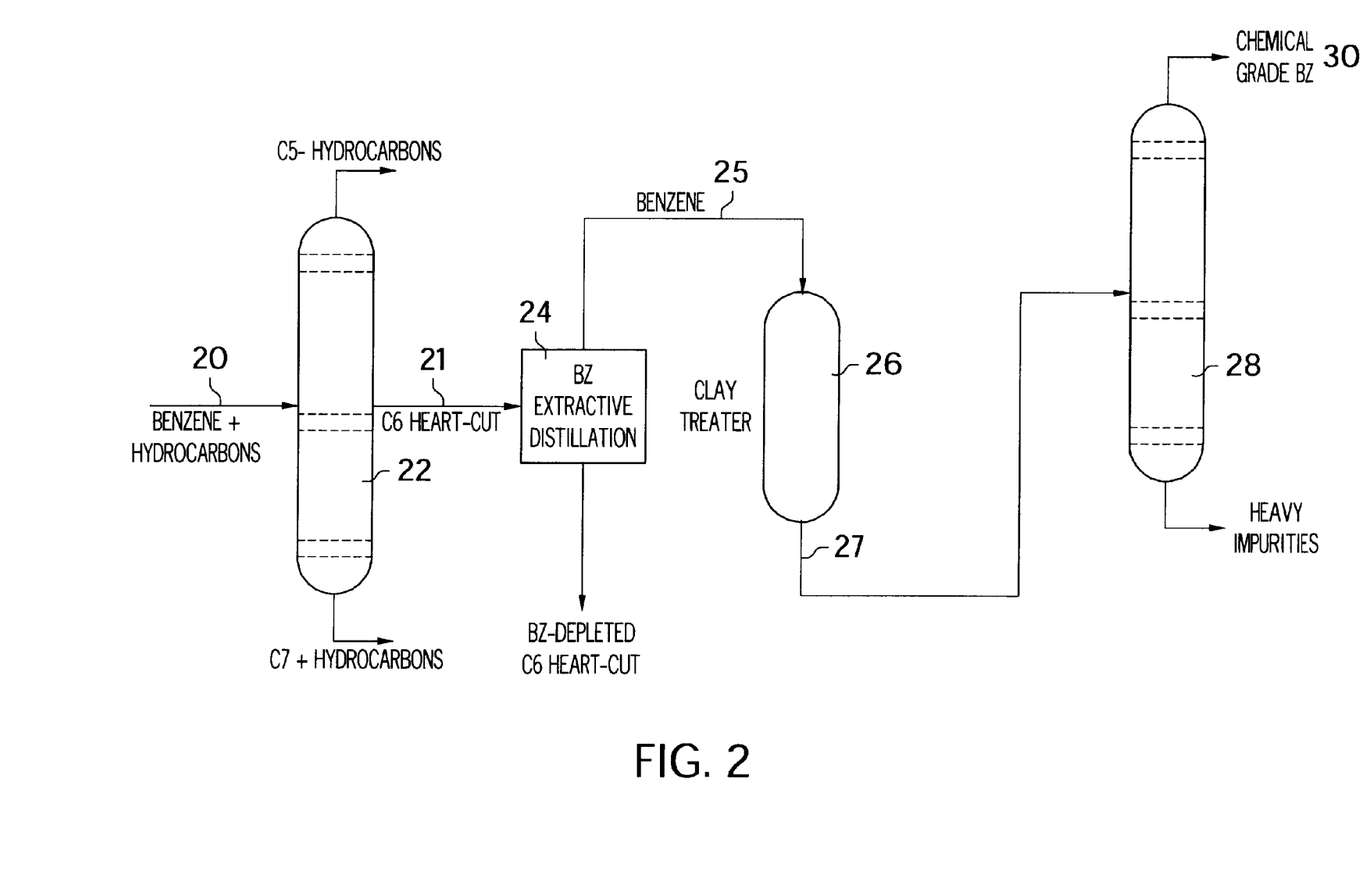
FIG. 2 is a flow diagram of a typical benzene extraction process.

FIG. 2 is a flow diagram of a typical process for obtaining a high purity (up to about 99.98%) benzene product. The process requires (1) a first column for removing heavies from a feed stream (22); (2) a benzene extractive distillation column (24); (3) a clay treater (26) to remove olefin impurities from the benzene recovered using the extractive distillation column (24); and (4) a benzene/toluene distillation tower (28). Referring to FIG. 2, a feed stream 20 comprising in the range of from about 1 to about 5% benzene is fed to a first column 22 where heavies (C7+) are removed as bottoms. A heart-cut stream 21 having a concentration in the range of from about 30 to about 50% benzene produced by the first column 22 is fed to a second column 24, which may be a multi-stage extraction column or a solvent extractive distillation unit. A benzene-depleted raffinate is removed from the product stream in column 22, and an extract stream containing the benzene 25 is fed to a clay treater 26, in which olefin impurities are reacted out of the product stream. The product stream 27 from of the clay treater 26 is fed to a benzene-toluene distillation tower 28, which removes toluene and any remaining heavies, to produce in a high purity benzene product 30.

Figure 3:
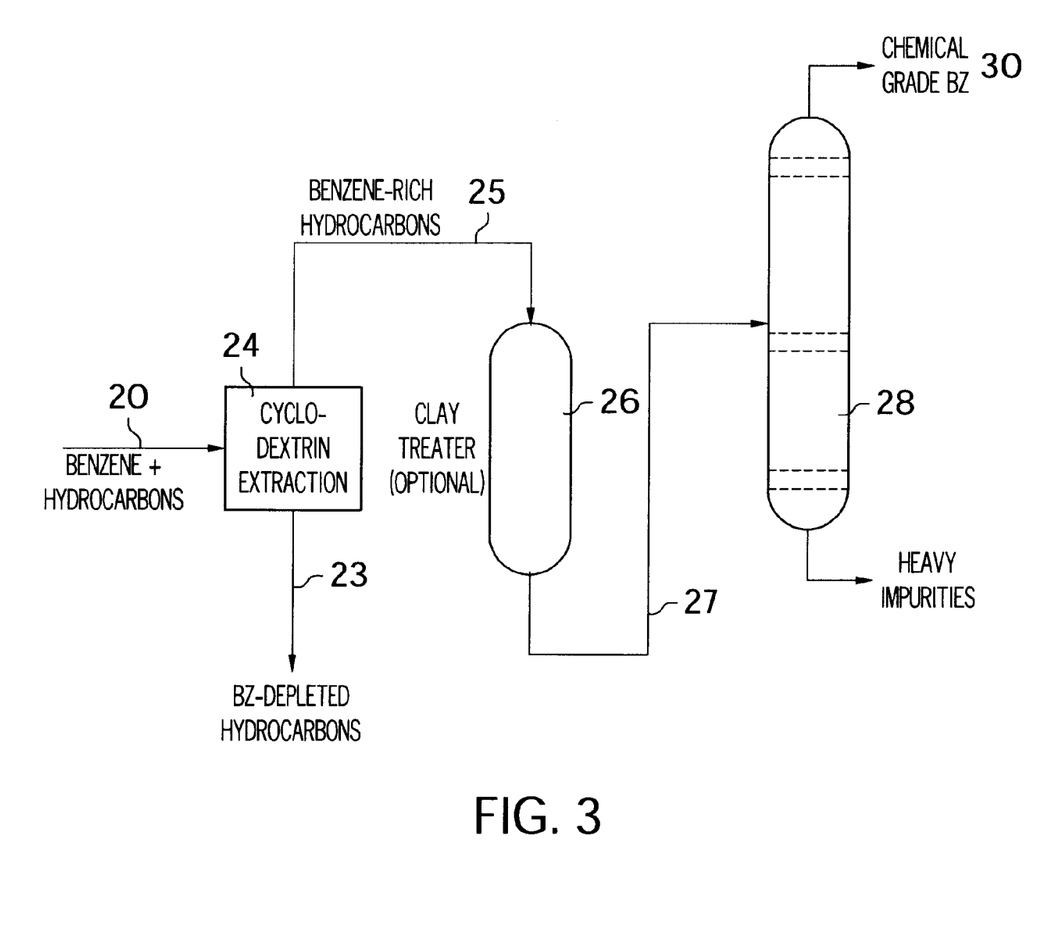
FIG. 3 is an flow diagram of an optional benzene extraction process according to the present invention.
Figure 4:
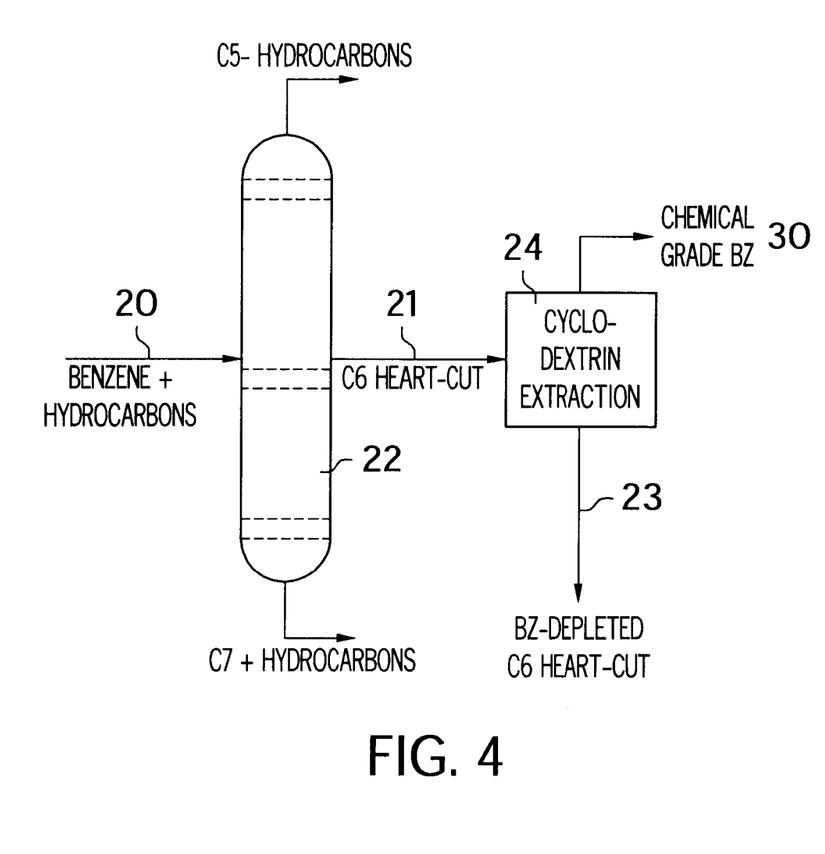
FIG. 4 is a flow diagram of another optional benzene extraction process according to the present invention.

Most applications do not require the high purity of benzene that can be produced using the the process depicted in FIG. 2. Because of this, it is preferable to use a process which is simpler and uses less equipment. FIGS. 3 and 4 depict preferred processes for using cyclodextrins to extract benzene using less equipment and at less expense than the process depicted in FIG. 2. The processes depicted in FIGS. 3 and 4 are capable of producing a product with a benzene concentration in the range of from about 60% to about 90%. Because some of the equipment in FIGS. 2, 3, and 4 is the same, like equipment will be given like numbers.

The process depicted in FIG. 3 is similar to the process depicted in FIG. 2 except that the first column 22 for removing heavies is omitted. A feed stream 20 comprising in the range of from about 1 to about 5% benzene is fed to a cyclodextrin unit 24 containing the cyclodextrin solution. The cyclodextrin complexes with the benzene in the feedstream 20, forming cyclodextrin/benzene complexes, which are immiscible in the remainder of the product stream. After separation, the cyclodextrin/benzene complexes are decomposed, e.g., by heating to a temperature in the range of from about 75° C. to about 110° C. The result of such decomposition is a lower aqueous layer consisting essentially of water and substituted CD's and an upper oily layer or vapor phase containing a high concentration of benzene. The upper oily layer or vapor phase is fed to a clay treater 26, where olefin impurities are reacted out of the product stream. The product stream 27 from of the clay treater 26 is fed to a benzene-toluene distillation tower 28, which removes toluene and any remaining heavies to produce a high concentration benzene product 30.

The process depicted in FIG. 4 also is similar to the process depicted in FIG. 2 except that FIG. 4 omits the clay treater 26 and the benzene/toluene distillation tower 28. Referring to FIG. 4, a feed stream 20 comprising in the range of from about 1% to about 5% benzene is fed to a first column 22 where heavies (C7+) are removed as bottoms. A heart-cut stream 21 in the range of from about 30% to about 50% benzene produced by the first column 22 is fed to a cyclodextrin unit 24. The cyclodextrin(s) complex with the benzene in the feedstream 20, forming cyclodextrin/benzene complexes. The benzene-depleted heart-cut 23 is removed from the cyclodextrin unit. The cyclodextrin/benzene complexes are decomposed into a lower aqueous layer consisting essentially of water and substituted CD's and an upper oily layer or vapor phase containing a high concentration of benzene, which is removed as a high concentration benzene product 30.

The invention will be better understood with reference to the following examples, which are illustrative only, and should not be construed as limiting the invention. In each of the following examples, all materials were obtained from Aldrich Chemical Co. unless otherwise noted.

EXAMPLE I

This example illustrates the selective encapsulation of benzene and paraffins by a C-6 substituted α-CD derivatives. A monoglucosyl-α-CD was obtained from CTD, Inc. (Gainsville, Fla.). The monoglucosyl-α-CD had a glucosyl group replacing the hydrogen atom of the primary —OH group in the C-6 position. The —OH groups in the C-2 and C-3 positions were not substituted.

In a sealed vial, an aqueous solution of 0.5057 g monoglucosyl-α-CD in 4.0998 g water was mixed with 0.3095 g of feed solution of 39.29% n-heptane, 0.50% cyclohexane, 3.93% benzene, 16.45% toluene, 4.33% EB, 4.39% PX, 9.77% MX, 4.30% OX, and 17.04% TMB. The vial was shaken vigorously at ambient conditions for two hours. No gel or precipitate formed. The upper hydrocarbon phase and the lower aqueous phase were separated and sampled, and the samples were analyzed using gas chromatography. The results are given in the following Table:

| Components | Feed, wt % | Hydrocarbon Phase, wt % | Recovered from CD, wt % | Selectivity |
|---|---|---|---|---|
| n-C7 | 39.29% | 35.10% | 72.27% | 0.84 |
| Cyclo-C6 | 0.50% | 0.34% | 2.92% | 0.20 |
| Bz | 3.93% | 2.91% | 5.06% | 1.00 |
| Tol | 16.45% | 16.93% | 8.39% | 3.51 |
| EB | 4.33% | 4.73% | 2.65% | 3.10 |
| PX | 4.39% | 4.70% | 5.11% | 1.60 |
| MX | 9.77% | 10.88% | 2.23% | 8.48 |
| OX | 4.30% | 4.81% | 0.51% | 16.40 |
| TMB | 17.04% | 19.59% | 0.86% | 39.60 |

The foregoing results demonstrate that n-heptane (a paraffin), cyclohexane (a naphthene), and benzene are more preferentially extracted by the C-6 substituted glucosyl-α-CD.

EXAMPLE II

This example illustrates the benzene-selective encapsulation by a randomly substituted β-CD derivative. The methyl-β-CD had an averaged degree of substitution of about 1.8. An aqueous solution of 0.5087 g M-β-CD in 4.0324 g water was mixed with 0.3012 g of feed solution in a sealed vial. The vial was shaken vigorously at ambient conditions for 2 hours. No gel or precipitate formed. The upper hydrocarbon phase and the lower aqueous phase were separated and sampled. The samples were analyzed using GC. The results are summarized in the following Table:

| Components | Feed, wt % | Hydrocarbon Phase, wt % | Recovered from CD, wt % | Selectivity |
|---|---|---|---|---|
| n-C7 | 39.29% | 41.44% | 7.95% | 42.71 |
| Cyclo-C6 | 0.50% | 0.34% | 2.17% | 1.48 |
| Bz | 3.93% | 2.47% | 20.24% | 1.00 |
| Tol | 16.45% | 14.96% | 37.68% | 3.25 |
| EB | 4.33% | 4.17% | 7.87% | 4.34 |
| PX | 4.39% | 4.32% | 6.17% | 5.74 |
| MX | 9.77% | 9.89% | 9.10% | 8.91 |
| OX | 4.30% | 4.26% | 5.78% | 6.04 |
| TMB | 17.04% | 18.15% | 3.04% | 48.92 |

The foregoing demonstrates that methyl-β-CD selectively encapsulated benzene over other paraffinic naphthenic, and aromatic compounds.

EXAMPLE III

This example illustrates the improvement in benzene-selective encapsulation due to the use of a mixed solvent. The methyl-β-CD used in this experiment again had an averaged degree of substitution of about 1.8. A mixed solvent of 40 wt % DMSO and 60 wt % water was prepared. A solution of 0.5064 g M-β-CD in 4.00158 g of the mixed solvent was mixed with 0.3066 g of feed solution in a sealed vial. The vial was shaken vigorously at ambient conditions for 2 hours. No gel or precipitate formed. The upper hydrocarbon phase and the lower aqueous phase were separated and sampled. The samples were analyzed using GC. The results are shown in the following Table:

| Components | Feed, wt % | Hydrocarbon Phase, wt % | Recovered from CD, wt % | Selectivity |
|---|---|---|---|---|
| n-C7 | 39.29% | 39.72% | 3.99% | 134.75 |
| Cyclo-C6 | 0.50% | 0.31% | 1.66% | 2.53 |
| Bz | 3.93% | 1.68% | 22.74% | 1.00 |
| Tol | 16.45% | 14.58% | 40.03% | 4.93 |
| EB | 4.33% | 4.43% | 7.05% | 8.51 |
| PX | 4.39% | 4.59% | 5.30% | 11.72 |
| MX | 9.77% | 10.43% | 8.95% | 15.77 |
| OX | 4.30% | 4.50% | 6.00% | 10.15 |
| TMB | 17.04% | 19.76% | 4.28% | 62.49 |

The foregoing results demonstrate that the mixed solvent of 40 wt % DMSO/60 wt % water significantly improved methyl-β-CD's selectivity toward benzene.

EXAMPLE IV

This example illustrates the benzene-selective encapsulation by another randomly substituted α-CD derivative. An aqueous solution of 0.5002 g hydroxypropyl-β-CD in 4.0211 g water is mixed with 0.3089 g of feed solution in a sealed vial. The vial was shaken vigorously at ambient conditions for 2 hours. No gel or precipitate formed. The upper hydrocarbon phase and the lower aqueous phase were separated and sampled. The samples were analyzed using GC. The results are shown in the following Table:

| Components | Feed, wt % | Hydrocarbon Phase, wt % | Recovered from CD, wt % | Selectivity |
|---|---|---|---|---|
| n-C7 | 39.29% | 40.20% | 6.93% | 50.57 |
| Cyclo-C6 | 0.50% | 0.39% | 1.54% | 2.21 |
| Bz | 3.93% | 2.69% | 23.45% | 1.00 |
| Tol | 16.45% | 15.48% | 39.75% | 3.39 |
| EB | 4.33% | 4.32% | 7.08% | 5.32 |
| PX | 4.39% | 4.45% | 5.43% | 7.14 |
| MX | 9.77% | 10.04% | 8.26% | 10.60 |
| OX | 4.30% | 4.37% | 5.17% | 7.37 |
| TMB | 17.04% | 18.06% | 2.39% | 65.87 |

The foregoing results demonstrate that HP-β-CD selectively encapsulated benzene over other paraffinic, naphthenic, and aromatic compounds.

EXAMPLE V

This example illustrates the improvement in benzene-selective encapsulation due to the use of a mixed solvent. A mixed solvent of 40 wt % DMSO and 60 wt % water was prepared. A solution of 0.5046 g HP-α-CD in 4.0007 g of the mixed solvent was mixed with 0.3268 g of feed solution in a sealed vial. The vial was shaken vigorously at ambient conditions for 2 hours. No gel or precipitate formed. The upper hydrocarbon phase and the lower aqueous phase were separated and sampled. The samples were analyzed using GC. The results are shown in the following Table:

| Components | Feed, wt % | Hydrocarbon Phase, wt % | Recovered from CD, wt % | Selectivity |
|---|---|---|---|---|
| n-C7 | 39.29% | 40.07% | 2.19% | 221.10 |
| Cyclo-C6 | 0.50% | 0.39% | 1.10% | 4.28 |
| Bz | 3.93% | 2.24% | 27.07% | 1.00 |
| Tol | 16.45% | 15.10% | 40.83% | 4.47 |
| EB | 4.33% | 4.42% | 6.16% | 8.67 |
| PX | 4.39% | 4.52% | 4.73% | 11.55 |
| MX | 9.77% | 10.17% | 8.49% | 14.48 |
| OX | 4.30% | 4.42% | 5.52% | 9.68 |
| TMB | 17.04% | 18.67% | 3.91% | 57.70 |

The foregoing results demonstrate that the mixed solvent of 40 wt % DMSO/60 wt % water significantly improved HP-β-CD's selectivity toward benzene.

Persons of ordinary skill in the art will recognize that many modifications may be made to the present invention without departing from the spirit and scope of the present invention. The embodiments described herein are meant to be illustrative only and should not be taken as limiting the invention, which is defined in the following claims.

I claim:

1. A method for separating benzene from other organic materials in a feed stream, the method comprising:
   providing a feed stream comprising benzene and at least one other organic material;
   treating said feed stream with at least one cyclodextrin in liquid phase in an amount and under conditions effective to selectively form immiscible complexes of said cyclodextrin and at least a portion of said benzene; and,
   separating said immiscible complexes from said feed stream.

2. The method of claim 1 wherein said providing a feed stream comprising benzene and at least one other organic material comprises separating a first stream comprising a first concentration of benzene into said feed stream comprising a second concentration of benzene greater than said first concentration and a bottoms comprising organic material heavier than benzene.

3. The method of claim 1 wherein said feed stream comprises a second concentration of benzene and wherein separating said complexes from said feed stream comprises:
dissociating said benzene from said immiscible complexes, producing an intermediate benzene stream having a third concentration of benzene greater than said second concentration;
removing olefin impurities from said intermediate benzene stream; and
removing substituted benzenes from said intermediate benzene stream, producing a benzene product stream having a fourth concentration of benzene greater than said third concentration.

4. The method of claim 2 wherein said separating said complexes from said feed stream comprises:
dissociating said benzene from said immiscible complexes, producing an intermediate benzene stream having a third concentration of benzene greater than said second concentration;
removing olefin impurities from said intermediate benzene stream; and
removing substituted benzenes from said intermediate benzene stream, producing a benzene product stream having a fourth concentration of benzene greater than said third concentration.

5. The method of claim 1 wherein said at least one other organic material comprises hydrocarbons in the gasoline boiling range selected from the group consisting of reformate, hydrocrackate, pyrolysis gasoline, fluid catalytic cracker naptha, and a combination thereof.

6. The method of claim 1 wherein said at least one other organic material comprises reformate.

7. The method of claim 2 wherein said at least one other organic material comprises hydrocarbons in the gasoline boiling range selected from the group consisting of reformate, hydrocrackate, pyrolysis gasoline, fluid catalytic cracker naptha, and a combination thereof.

8. The method of claim 2 wherein said at least one other organic material comprises reformate.

9. A method for separating benzene from other organic materials in a feed stream, the method comprising:
providing a feed stream comp rising benzene and at least one other organic material;
treating said feed stream with at least one cyclodextrin in liquid phase in an amount and under conditions effective to selectively form immiscible complexes of said cyclodextrin and at least a portion of said benzene, wherein said cyclodextrin is selected from the group consisting of α-, β-, and γ-cyclodextrins comprising a primary hydroxyl group at a C-6 position which either is unsubstituted or substituted or by a member selected from the group consisting of glucosyl groups, maltosyl groups, maltooligosaccharride residues, hydroxyalkyl groups, sulfur-containing groups, carboxyalkyl groups, methyl groups, acylated groups, silyl groups, halogenated groups, nitrogen-containing groups, inorganic acid esters; and,
separating said immiscible complexes from said feed stream.

10. The method of claim 1 wherein said cyclodextrin is selected from the group consisting of α-, β-, and γ-cyclodextrins comprising a hydroxyl group substituted at a position selected from the group consisting of the C-2, the C-3, and the C-6 position by a member selected from the group consisting of glucosyl groups, maltosyl groups, maltooligosaccharride residues, hydroxyalkyl groups, sulfur-containing groups, carboxyalkyl groups, methyl groups, acylated groups, silyl groups, halogenated groups, nitrogen-containing groups, inorganic acid esters.

11. The method of claim 2 wherein said cyclodextrin is selected from the group consisting of α-, β-, and γ-cyclodextrins comprising a primary hydroxyl group at a C-6 position substituted by a member selected from the group consisting of glucosyl groups, maltosyl groups, maltooligosaccharride residues, hydroxyalkyl groups, sulfur-containing groups, carboxyalkyl groups, methyl groups, acylated groups, silyl groups, halogenated groups, nitrogen-containing groups, inorganic acid esters.

12. The method of claim 3 wherein said cyclodextrin is selected from the group consisting of α-, β-, and γ-cyclodextrins comprising a primary hydroxyl group at a C-6 position substituted by a member selected from the group consisting of glucosyl groups, maltosyl groups, maltooligosaccharride residues, hydroxyalkyl groups, sulfur-containing groups, carboxyalkyl groups, methyl groups, acylated groups, silyl groups, halogenated groups, nitrogen-containing groups, inorganic acid esters.

13. The method of claim 5 wherein said cyclodextrin is selected from the group consisting of α-, β-, and γ-cyclodextrins comprising a primary hydroxyl group at a C-6 position substituted by a member selected from the group consisting of glucosyl groups, maltosyl groups, maltooligosaccharride residues, hydroxyalkyl groups, sulfur-containing groups, carboxyalkyl groups, methyl groups, acylated groups, silyl groups, halogenated groups, nitrogen-containing groups, inorganic acid esters.

14. The method of claim 6 wherein said cyclodextrin is selected from the group consisting of α-, β-, and γ-cyclodextrins comprising a primary hydroxyl group at a C-6 position substituted by a member selected from the group consisting of glucosyl groups, maltosyl groups, maltooligosaccharride residues, hydroxyalkyl groups, sulfur-containing groups, carboxyalkyl groups, methyl groups, acylated groups, silyl groups, halogenated groups, nitrogen-containing groups, inorganic acid esters.

15. The method of claim 7 wherein said cyclodextrin is selected from the group consisting of α-, β-, and γ-cyclodextrins comprising a primary hydroxyl group at a C-6 position substituted by a member selected from the group consisting of glucosyl groups, maltosyl groups, maltooligosaccharride residues, hydroxyalkyl groups, sulfur-containing groups, carboxyalkyl groups, methyl groups, acylated groups, silyl groups, halogenated groups, nitrogen-containing groups, inorganic acid esters.

16. The method of claim 8 wherein said cyclodextrin is selected from the group consisting of α-, β-, and γ-cyclodextrins comprising a primary hydroxyl group at a C-6 position substituted by a member selected from the group consisting of glucosyl groups, maltosyl groups, maltooligosaccharride residues, hydroxyalkyl groups, sulfur-containing groups, carboxyalkyl groups, methyl groups, acylated groups, silyl groups, halogenated groups, nitrogen-containing groups, inorganic acid esters.

17. The method of claim 1 further comprising
dissociating said benzene from said cyclodextrin; and,
collecting said benzene.

18. The method of claim 2 further comprising
dissociating said benzene from said cyclodextrin; and,
collecting said benzene.

19. The method of claim 3 further comprising
collecting said benzene.

20. The method of claim 5 further comprising
dissociating said benzene from said cyclodextrin; and,
collecting said benzene.

21. The method of claim 6 further comprising
dissociating said benzene from said cyclodextrin; and,
collecting said benzene.

22. The method of claim 7 further comprising
dissociating said benzene from said cyclodextrin; and,
collecting said benzene.

23. The method of claim 8 further comprising
dissociating said benzene from said cyclodextrin; and,
collecting said benzene.

24. A complex comprising benzene encapsulated by a cyclodextrin in liquid phase selected from the group consisting of α-, β-, and γ-cyclodextrins comprising a primary hydroxyl group at a C-6 position which either is unsubstituted or which is substituted by a member selected from the group consisting of glucosyl groups, maltosyl groups, maltooligosaccharide residues, hydroxyalkyl groups, sulfur-containing groups, carboxyalkyl groups, methyl groups, acylated groups, silyl groups, halogenated groups, nitrogen-containing groups, and inorganic acid esters.

25. The complex of claim 24 wherein said cyclodextrin is selected from the group consisting of α-, β-, and γ-cyclodextrins comprising a primary hydroxyl group at a C-6 position substituted by a member selected from the group consisting of glucosyl groups, maltosyl groups, maltooligosaccharride residues, hydroxyalkyl groups, sulfur-containing groups, carboxyalkyl groups, methyl groups, acylated groups, silyl groups, halogenated groups, nitrogen-containing groups, inorganic acid esters.

26. The complex of claim 25 disposed in a mixture comprising organic materials in the gasoline boiling range selected from the group consisting of reformate, hydrocrackate, pyrolysis gasoline, fluid catalytic cracker naptha, one or more solvents, and combinations thereof.

27. The complex of claim 24 disposed in a mixture comprising organic materials in the gasoline boiling range selected from the group consisting of reformate, hydrocrackate, pyrolysis gasoline, fluid catalytic cracker naptha, one or more solvents, and combinations thereof.

28. A method for separating benzene from other organic materials in a feed stream, the method comprising:
providing a feed stream comprising benzene and at least one other organic material;
treating said feed stream with at least one cyclodextrin in liquid phase in an amount and under conditions effective to selectively form immiscible complexes of said cyclodextrin and at least a portion of said benzene, said cyclodextrin being selected from the group consisting of α-, β-, and γ-derivatives of cyclodextrin which comprises a primary hydroxyl group at a C-6 position which either is unsubstituted or which bears a substituent effective at least to maintain selectivity to benzene equivalent to said cyclodextrins which are unsubstituted on said primary hydroxyl group at said C-6 position; and
separating said immiscible complexes from said feed stream.

29. A method for separating benzene from other organic materials in a feed stream, the method comprising:
providing a feed stream comprising benzene and at least one other organic material comprising hydrocarbons in the gasoline boiling range selected from the group consisting of reformate, hydrocrackate, pyrolysis gasoline, fluid catalytic cracker naphtha, and a combination thereof;
treating said feed stream with at least one cyclodextrin in liquid phase in an amount and under conditions effective to selectively form immiscible complexes of said cyclodextrin and at least a portion of said benzene; and,
separating said immiscible complexes from said feed stream.

30. The method of claim 29 wherein said at least one other organic material comprises reformate.

31. The method of claim 28 wherein said at least one other organic material comprises hydrocarbons in the gasoline boiling range selected from the group consisting of reformate, hydrocrackate, pyrolysis gasoline, fluid catalytic cracker naphtha, and a combination thereof.

32. The method of claim 31 wherein said at least one other organic material comprises reformate.

33. The method of claim 28 further comprising
dissociating said benzene from said cyclodextrin; and,
collecting said benzene.

34. The method of claim 29 further comprising
dissociating said benzene from said cyclodextrin; and,
collecting said benzene.

35. The method of claim 30 further comprising
dissociating said benzene from said cyclodextrin; and,
collecting said benzene.

36. The method of claim 31 further comprising
dissociating said benzene from said cyclodextrin; and,
collecting said benzene.

37. The method of claim 32 further comprising
dissociating said benzene from said cyclodextrin; and,
collecting said benzene.

38. A method for separating benzene from other organic materials in a feed stream, the method comprising:
providing a feed stream comprising benzene and an organic material selected from the group consisting of aromatics, multi-branched paraffins, multi-branched olefins, 1–2 and 2–3 substituted naphthenes, and combinations thereof, and,
treating said feed stream with unsubstituted α-cyclodextrin in liquid phase in an amount and under conditions effective to selectively form immiscible complexes of said cyclodextrin and at least a portion of said benzene; and,
separating said immiscible complexes from said stream.

39. A method for separating benzene from other organic materials in a feed stream, the method comprising:

providing a feed stream comprising benzene and an organic material selected from the group consisting of paraffins, naphthenes, olefins, aromatics, and combinations thereof; and, treating said feed stream with a cyclodextrin in liquid phase in an amount and under conditions effective to selectively form immiscible complexes of said cyclodextrin and at least a portion of said benzene, wherein said cyclodextrin is selected from the group consisting of unsubstituted β- and γ-cyclodextrins and β- and γ-cyclodextrins comprising a substituent on a primary hydroxyl group at a C-6 position which is effective at least to maintain selectivity to benzene to a level equivalent to said unsubstituted β- and γ-cyclodextrins; and, separating said immiscible complexes from said feed stream.

40. A method for separating benzene from other organic materials in a feed stream, the method comprising:

providing a feed stream comprising benzene and gasoline;

treating said feed stream with a cyclodextrin in liquid phase in an amount and under conditions effective to selectively form immiscible complexes of said cyclodextrin and at least a portion of said benzene, wherein said cyclodextrin is selected from the group consisting of unsubstituted β- and γ-cyclodextrins and β- and γ-cyclodextrins comprising a substituent on a primary hydroxyl group at a C-6 position selected from the group consisting of glucosyl groups, maltosyl groups, maltooligosaccharide residues, hydroxyalkyl groups, sulfur-containing groups, carboxyalkyl groups, methyl groups, acylated groups, silyl groups, halogenated groups, nitrogen-containing groups, inorganic esters; and, separating said immiscible complexes from said feed stream.

41. The method of claim 9 wherein said feed stream is in liquid phase.

42. The method of claim 28 wherein said feed stream is in liquid phase.

43. The method of claim 30 wherein said feed stream is in liquid phase.

44. The method of claim 40 wherein said feed stream is in liquid phase.

45. The method of claim 1 wherein said liquid phase is an aqueous phase.

46. A method for separating benzene from other organic materials in a feed stream, the method comprising:

providing a liquid feed stream comprising benzene and at least one other organic material;

treating said feed stream with at least one cyclodextrin in liquid phase in an amount and under conditions effective to form immiscible complexes of said cyclodextrin and at least a portion of said benzene; and, separating said immiscible complexes from said feed stream.

47. A method for separating benzene from other organic materials in a feed stream, the method comprising:

providing a liquid feed stream comprising at least a first and a second organic material;

treating said feed stream with at least one cyclodextrin in liquid phase in an amount and under conditions effective to selectively form immiscible complexes of said cyclodextrin with at least a portion of said first organic material; and, separating said immiscible complexes from said feed stream.

* * * * *